US011963810B2

(12) United States Patent
Taki

(10) Patent No.: US 11,963,810 B2
(45) Date of Patent: Apr. 23, 2024

(54) ESTIMATION DEVICE, ESTIMATION METHOD, AND ESTIMATION PROGRAM

(71) Applicant: FUJIFILM CORPORATION, Tokyo (JP)

(72) Inventor: Tomoko Taki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 276 days.

(21) Appl. No.: 17/591,617

(22) Filed: Feb. 3, 2022

(65) Prior Publication Data
US 2022/0287666 A1 Sep. 15, 2022

(30) Foreign Application Priority Data
Mar. 12, 2021 (JP) .................................. 2021-040687

(51) Int. Cl.
G06N 3/08 (2023.01)
A61B 6/00 (2006.01)
(Continued)

(52) U.S. Cl.
CPC .............. A61B 6/482 (2013.01); A61B 6/032 (2013.01); A61B 6/483 (2013.01); A61B 6/505 (2013.01);
(Continued)

(58) Field of Classification Search
CPC ......... A61B 6/482; A61B 6/032; A61B 6/483; A61B 6/505; G06N 3/08; G06T 7/0012;
(Continued)

(56) References Cited

U.S. PATENT DOCUMENTS 7,545,965 B2  6/2009 Suzuki et al.
2018/0263559 A1* 9/2018 Kawamura ............ A61B 6/032

FOREIGN PATENT DOCUMENTS

JP   2018-153605 A    10/2018
WO  2019/208037 A1   10/2019

OTHER PUBLICATIONS

Naoki Nakanishi et al. "Preliminary investigation on decomposition of individual muscles and bones of lower extremity from single radiograph using CycleGAN", Technical Report of IEICE, The Institute of Electronics, Information and Communication Engineers, Aug. 28, 2019.
(Continued)

Primary Examiner — David P Porta
Assistant Examiner — Fani Polyzos Boosalis
(74) Attorney, Agent, or Firm — SOLARIS Intellectual Property Group, PLLC

(57) ABSTRACT

An estimation device includes at least one processor, in which the processor functions as a learned neural network that derives a result of estimation of at least one emphasis image in which a specific composition of a subject including a plurality of compositions is emphasized from a simple two-dimensional image acquired by simply imaging the subject. The learned neural network is learned by using, as teacher data, a composite two-dimensional image representing the subject, which is derived by combining a three-dimensional CT image of the subject, and an emphasis image for learning in which the specific composition of the subject is emphasized, which is derived from the CT image.

7 Claims, 14 Drawing Sheets

(51) Int. Cl.
*A61B 6/03* (2006.01)
*A61B 6/50* (2024.01)
*G06T 7/00* (2017.01)

(52) U.S. Cl.
CPC ............. *G06N 3/08* (2013.01); *G06T 7/0012* (2013.01); *G06T 2207/10116* (2013.01); *G06T 2207/20081* (2013.01); *G06T 2207/20084* (2013.01); *G06T 2207/30008* (2013.01)

(58) Field of Classification Search
CPC . G06T 2207/10116; G06T 2207/20081; G06T 2207/20084; G06T 2207/30008
See application file for complete search history.

(56) References Cited

OTHER PUBLICATIONS

English language translation of the following: Notice dated Oct. 31, 2023 from the JPO in a Japanese patent application No. 2021-040687 corresponding to the instant patent application. This office action translation is submitted now in order to supplement the understanding of the cited references which are being disclosed in the instant Information Disclosure Statement.

* cited by examiner

ESTIMATION DEVICE, ESTIMATION METHOD, AND ESTIMATION PROGRAM

CROSS REFERENCE TO RELATED APPLICATIONS

The present application claims priority under 35 U.S.C. § 119 to Japanese Patent Application No. 2021-040687 filed on Mar. 12, 2021. The above application is hereby expressly incorporated by reference, in its entirety, into the present application.

BACKGROUND OF THE INVENTION

Technical Field

The present disclosure relates to an estimation device, an estimation method, and an estimation program.

Related Art

In the related art, energy subtraction processing using two radiation images obtained by irradiating a subject with two types of the radiation having different energy distributions by using an amount of attenuation of transmitted radiation different from each other depending on a substance configuring the subject is known. The energy subtraction processing is a method in which pixels of the two radiation images obtained as described above are associated with each other, and the pixels are multiplied by an appropriate weighting coefficient and then subtracted (subtract) to acquire an image obtained by emphasizing a specific structure. In addition, in addition to a bone part and a soft part, derivation of a composition of a human body, such as fat and muscle, in the soft part is performed by the energy subtraction processing (see JP2018-153605A).

In addition, various methods have been proposed in which the radiation image acquired by imaging the subject is used to derive a radiation image different from the acquired radiation image. For example, U.S. Pat. No. 7,545,965B proposes a method for using a learned model constructed by learning a neural network by using, as teacher data, a radiation image of a subject acquired by simple imaging and a bone part image of the same subject to derive the bone part image from the radiation image of the subject acquired by the simple imaging.

Note that the simple imaging is an imaging method for acquiring one two-dimensional image, which is a transmission image of the subject, by emitting the radiation to the subject once. In the following description, the two-dimensional image acquired by simple imaging will be referred to as a simple two-dimensional image.

However, it is desired to estimate an image in which a specific composition, such as a bone part, is emphasized with higher accuracy.

SUMMARY OF THE INVENTION

The present disclosure has been made in view of the above circumstances, and is to enable estimation of the image in which the specific composition is emphasized with high accuracy.

An aspect of the present disclosure relates to an estimation device comprising at least one processor, in which the processor functions as a learned neural network that derives a result of estimation of at least one emphasis image in which a specific composition of a subject including a plurality of compositions is emphasized from a simple two-dimensional image acquired by simply imaging the subject, and the learned neural network is learned by using, as teacher data, a composite two-dimensional image representing the subject, which is derived by combining a three-dimensional CT image of the subject, and an emphasis image for learning in which the specific composition of the subject is emphasized, which is derived from the CT image.

Note that in the estimation device according to the present disclosure, the composite two-dimensional image may be derived by deriving an attenuation coefficient of radiation for a composition at each position on a three-dimensional space, and projecting the CT image in a predetermined direction based on the attenuation coefficient.

In addition, the estimation device according to the present disclosure, the emphasis image for learning may be derived by specifying a region of the specific composition in the CT image and projecting the CT image having the region of the specific composition in a predetermined direction.

In addition, the estimation device according to the present disclosure, the emphasis image for learning may be derived by performing weighting subtraction on two composite two-dimensional images simulating imaging of the subject with radiation having different energy distributions, which are derived by projecting the CT image in a predetermined direction.

In addition, the estimation device according to the present disclosure, the specific composition may be at least one of a soft part, a bone part, a muscle, or a fat of the subject.

Another aspect of the present disclosure relates to an estimation method comprising using a learned neural network that derives a result of estimation of at least one emphasis image in which a specific composition of a subject including a plurality of compositions is emphasized from a simple radiation image acquired by simply imaging the subject to derive the at least one emphasis image in which the specific composition of the subject is emphasized from the simple radiation image, in which the learned neural network is learned by using, as teacher data, a composite two-dimensional image representing the subject, which is derived by combining a three-dimensional CT image of the subject, and an emphasis image for learning in which the specific composition of the subject is emphasized, which is derived from the CT image.

Note that the estimation method according to the present disclosure may be provided as a program causing a computer to execute.

According to the present disclosure, it is possible to estimate image in which the specific composition is emphasized with high accuracy.

DETAILED DESCRIPTION

Figure 1:
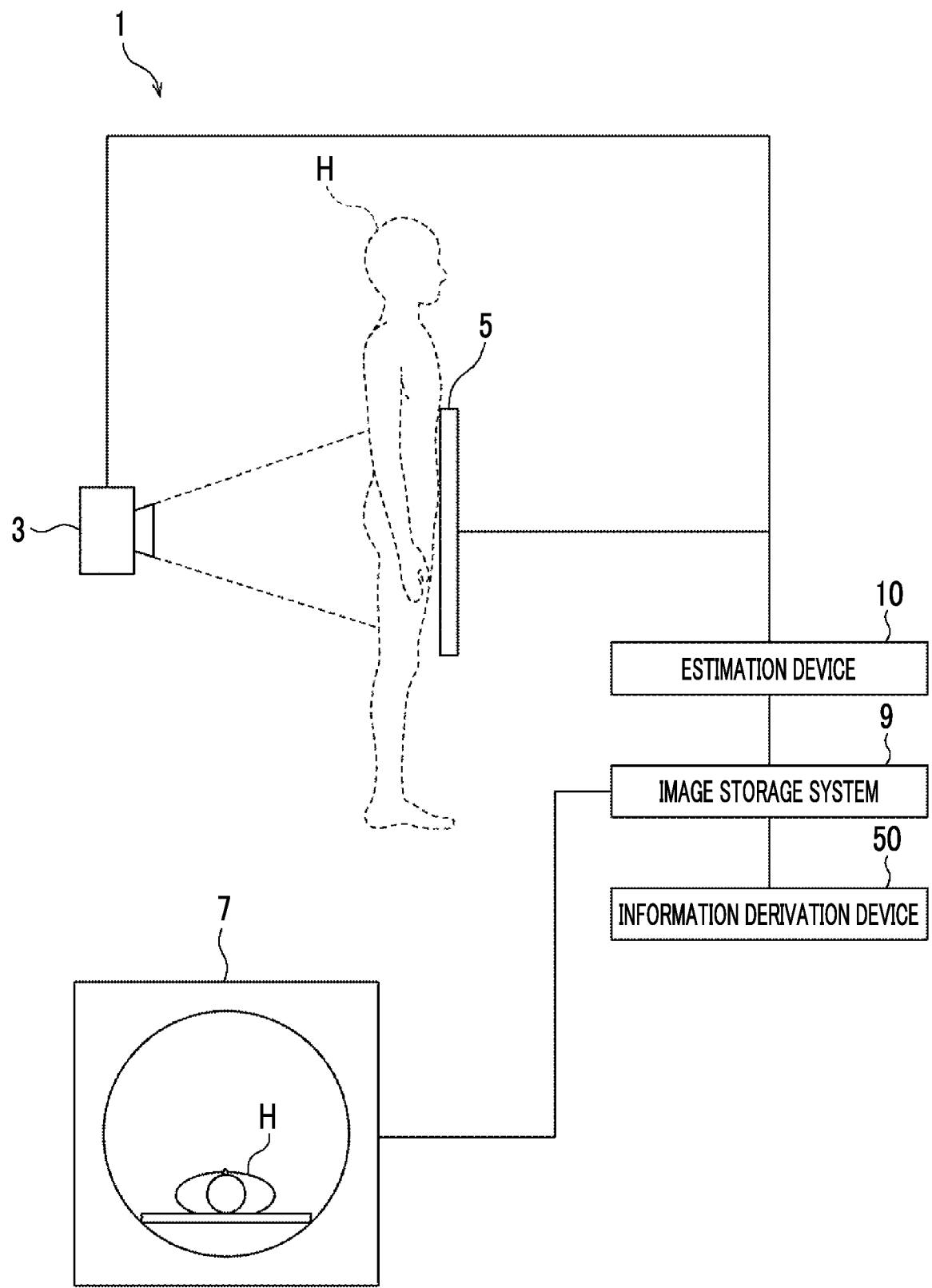
FIG. 1 is a schematic block diagram showing a configuration of a radiography system to which an estimation device according to a first embodiment of the present disclosure is applied.

Hereinafter, embodiments of the present disclosure will be described with reference to the drawings. FIG. 1 is a schematic block diagram showing a configuration of a radiography system to which an estimation device according to a first embodiment of the present disclosure is applied. As shown in FIG. 1, the radiography system according to the first embodiment comprises an imaging apparatus 1, a computed tomography (CT) device 7, an image storage system 9, an estimation device 10 according to the first embodiment, and an information derivation device 50. The imaging apparatus 1, the CT device 7, the estimation device 10, and the information derivation device 50 are connected to the image storage system 9 via a network (not shown).

The imaging apparatus 1 is an imaging apparatus capable of acquiring a simple radiation image G0 of a subject H by irradiating the radiation detector 5 with radiation, such as X-rays, emitted from the radiation source 3 and transmitted through the subject H. The acquired simple radiation image G0 is input to the estimation device 10. The simple radiation image G0 is, for example, a front image including the vicinity of the crotch of the subject H.

The radiation detector 5 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

The CT device 7 acquires a plurality of tomographic images representing a plurality of tomographic surfaces of the subject H as a three-dimensional CT image V0 by performing CT imaging on the subject H. The CT value of each pixel (voxel) in the CT image is a numerical value of the radiation absorbance in the composition constituting the human body. The CT value will be described below.

The image storage system 9 is a system that stores the image data of the radiation image acquired by the imaging apparatus 1 and the image data of the CT image acquired by the CT device 7. The image storage system 9 extracts an image corresponding to requests from the estimation device 10 and the information derivation device 50 from the stored radiation image and CT image and transmits the extracted image to a request source device. Specific examples of the image storage system 9 include picture archiving and communication systems (PACS). Note that in the present embodiment, the image storage system 9 stores a large amount of teacher data for learning the neural network described below.

Figure 2:
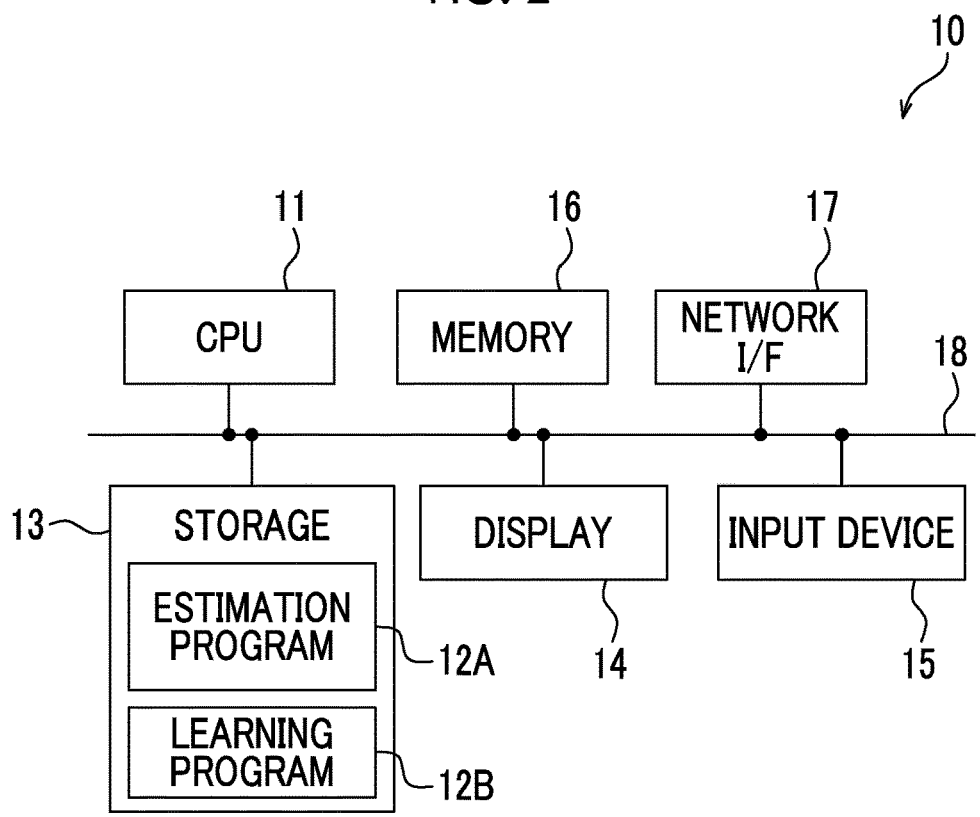
FIG. 2 is a diagram showing a schematic configuration of the estimation device according to the first embodiment.

Then, the estimation device according to the first embodiment will be described. First, a hardware configuration of the estimation device according to the first embodiment will be described with reference to FIG. 2. As shown in FIG. 2, the estimation device 10 is a computer, such as a workstation, a server computer, and a personal computer, and comprises a central processing unit (CPU) 11, a non-volatile storage 13, and a memory 16 as a transitory storage region. In addition, the estimation device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. Note that the CPU 11 is an example of a processor according to the present disclosure.

The storage 13 is realized by a hard disk drive (HDD), a solid state drive (SSD), a flash memory, and the like. The storage 13 as a storage medium stores an estimation program 12A and a learning program 12B installed in the estimation device 10. The CPU 11 reads out the estimation program 12A and the learning program 12B from the storage 13, expands the estimation program 12A and the learning program 12B in the memory 16, and executes the expanded estimation program 12A and the expanded learning program 12B.

Note that the estimation program 12A and the learning program 12B are stored in a storage device of the server computer connected to the network or in a network storage in a state of being accessible from the outside, and are downloaded and installed in the computer that configures the estimation device 10 in response to the request. Alternatively, the estimation program 12A and the learning program 12B are distributed in a state of being recorded on a recording medium, such as a digital versatile disc (DVD) or a compact disc read only memory (CD-ROM), and are installed in the computer that configures the estimation device 10 from the recording medium.

Figure 3:
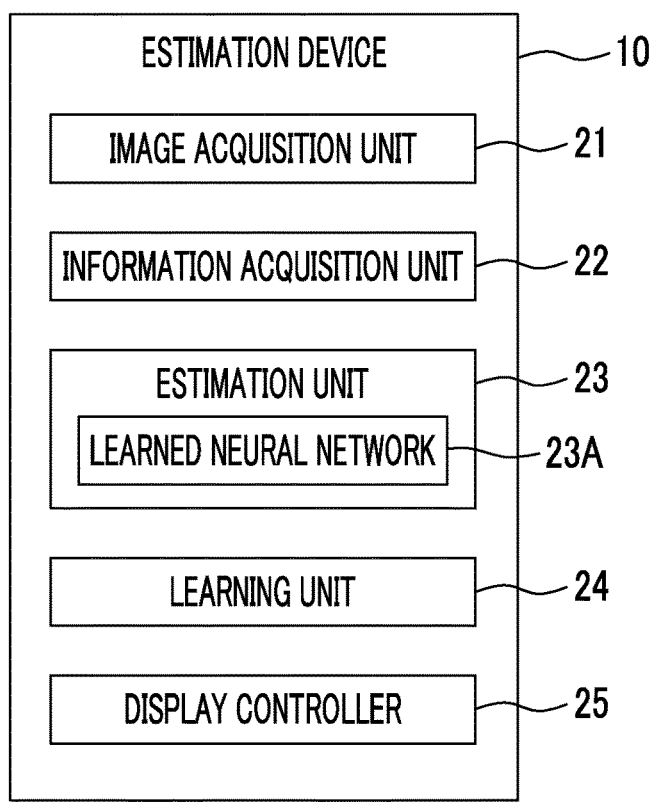
FIG. 3 is a diagram showing a functional configuration of an estimation device according to the first embodiment.

Then, a functional configuration of the estimation device according to the first embodiment will be described. FIG. 3 is a diagram showing the functional configuration of the estimation device according to the first embodiment. As shown in FIG. 3, the estimation device 10 comprises an image acquisition unit 21, an information acquisition unit 22, an estimation unit 23, a learning unit 24, and a display controller 25. Further, the CPU 11 functions as the image acquisition unit 21, the information acquisition unit 22, the estimation unit 23, and the display controller 25 by executing the estimation program 12A. In addition, the CPU 11 functions as the learning unit 24 by executing the learning program 12B.

The image acquisition unit 21 acquires the simple radiation image G0 which is the front image of the vicinity of the crotch of the subject H from the radiation detector 5 by causing the imaging apparatus 1 to perform the simple imaging of the subject H. In a case in which the simple radiation image G0 are acquired, an imaging conditions, such as an imaging dose, a radiation quality, a tube voltage, a source image receptor distance (SID) which is a distance between the radiation source 3 and the surface of the radiation detector 5, a source object distance (SOD) which is a distance between the radiation source 3 and a surface of the subject H, and the presence or absence of a scattered ray removal grid are set.

The imaging conditions need only be set by input from the input device 15 by an operator. The set imaging conditions are stored in the storage 13. The simple radiation image G0 and the imaging conditions are also transmitted to and stored in the image storage system 9.

Note that in the present embodiment, the simple radiation image G0 may be acquired by a program separate from the estimation program 12A and stored in the storage 13. In this case, the image acquisition unit 21 acquires the simple radiation image G0 stored in the storage 13 by reading out the simple radiation image G0 from the storage 13 for processing.

The information acquisition unit 22 acquires the teacher data for learning a neural network, which will be described below, from the image storage system 9 via the network I/F 17.

The estimation unit 23 derives the results of estimation of the bone part image in which the bone part is emphasized and the soft part image in which the soft part is emphasized included in the subject H from the simple radiation image G0. Therefore, the estimation unit 23 derives the results of estimation of the bone part image and the soft part image by using a learned neural network 23A that outputs the bone part image and the soft part image in a case in which the simple radiation image G0 is input. Note that in the present embodiment, a target for deriving the results of estimation of the bone part image and the soft part image is an image of the vicinity of the hip joint of the subject H, but the present disclosure is not limited to this. In addition, the bone part image and the soft part image derived by the estimation unit 23 are examples of an emphasis image.

The learning unit 24 constructs the learned neural network 23A by machine learning the neural network by using the teacher data. Examples of the neural network include a simple perceptron, a multi-layer perceptron, a deep neural network, a convolutional neural network, a deep belief network, a recurrent neural network, and a stochastic neural network. In the present embodiment, the convolutional neural network is used as the neural network.

Figure 4:
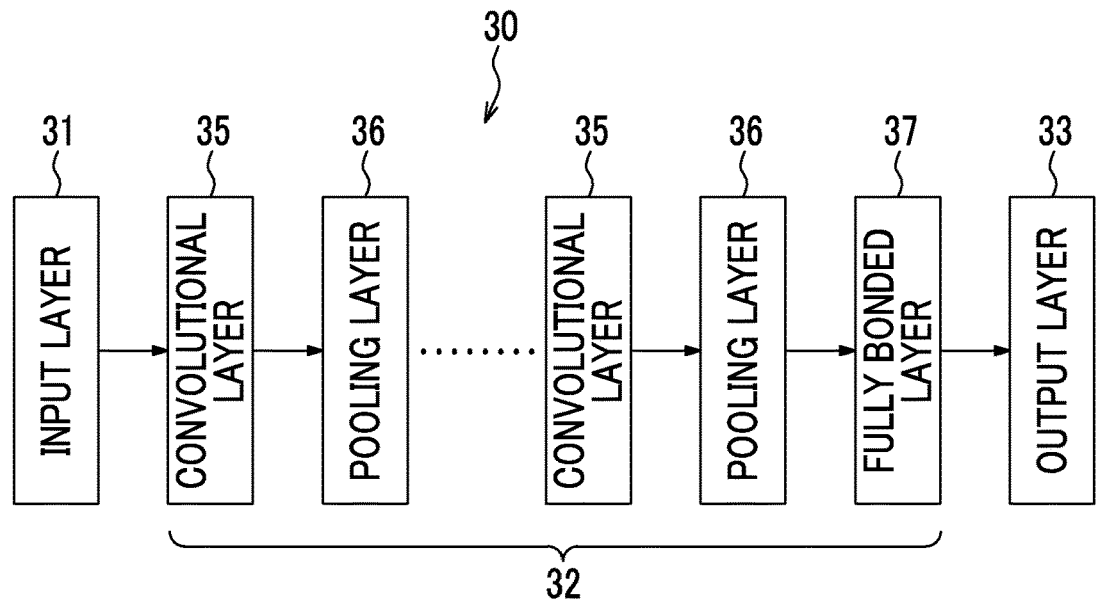
FIG. 4 is a diagram showing a schematic configuration of a neural network used in the present embodiment.

FIG. 4 is a diagram showing the neural network used in the present embodiment. As shown in FIG. 4, a neural network 30 comprises an input layer 31, an interlayer 32, and an output layer 33. The interlayer 32 comprises, for example, a plurality of convolutional layers 35, a plurality of pooling layers 36, and a fully bonded layer 37. In the neural network 30, the fully bonded layer 37 is present in front of the output layer 33. Further, in the neural network 30, the convolutional layer 35 and the pooling layer 36 are alternately disposed between the input layer 31 and the fully bonded layer 37.

Note that a configuration of the neural network 30 is not limited to the example of FIG. 4. For example, the neural network 30 may comprise one convolutional layer 35 and one pooling layer 36 between the input layer 31 and the fully bonded layer 37.

Figure 5:
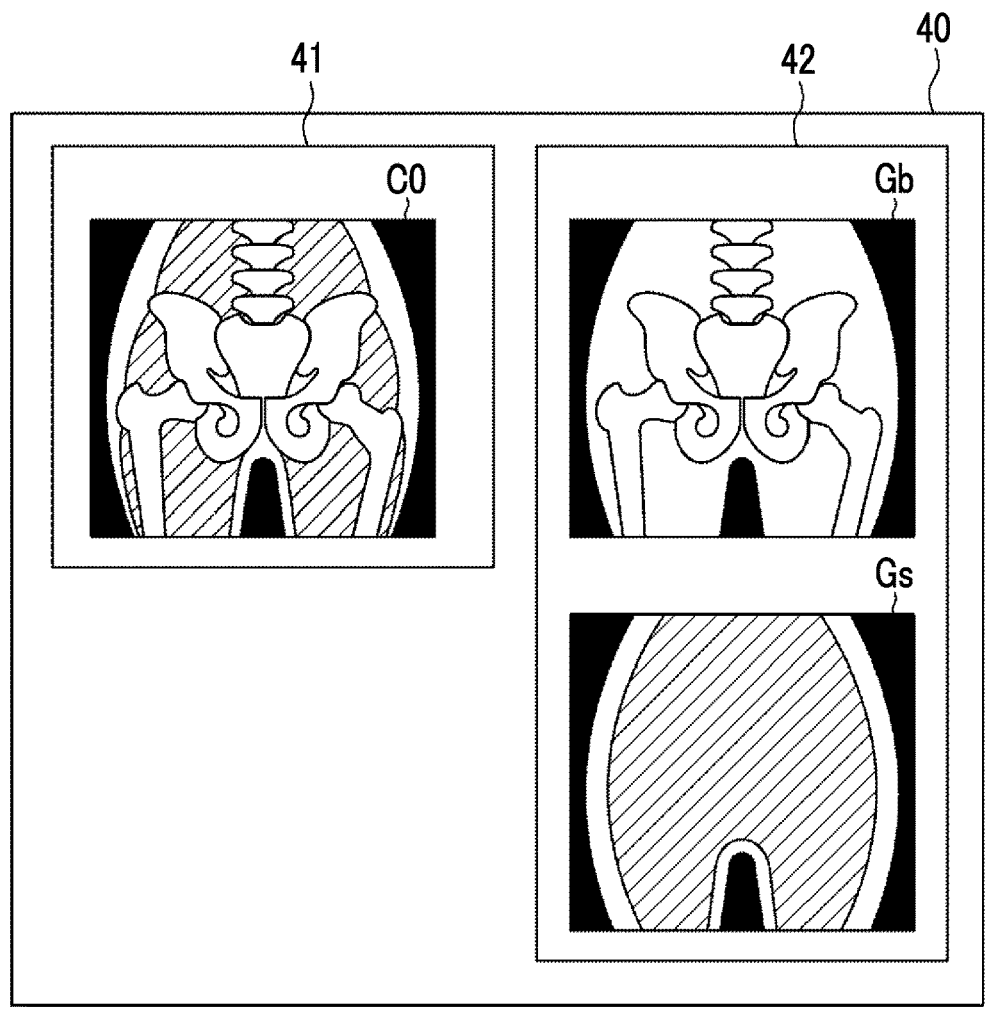
FIG. 5 is a diagram showing teacher data.

FIG. 5 is a diagram showing an example of the teacher data used for learning the neural network. As shown in FIG. 5, teacher data 40 consists of learning data 41 and correct answer data 42. In the present embodiment, the data input to the learned neural network 23A to obtain the result of estimation of the bone density is the simple radiation image G0, but the learning data 41 includes a composite two-dimensional image C0 representing the subject H derived by combining the CT image V0.

The correct answer data 42 is the bone part image Gb and the soft part image Gs in the vicinity of the target bone (that is, a femur) of the subject from which the learning data 41 is acquired. The bone part image Gb and the soft part image Gs, which are the correct answer data 42, are derived from the CT image V0 by the information derivation device 50. Hereinafter, the information derivation device 50 will be described. The bone part image Gb and the soft part image Gs derived from the CT image V0 are examples of an emphasis image for learning.

Figure 6:
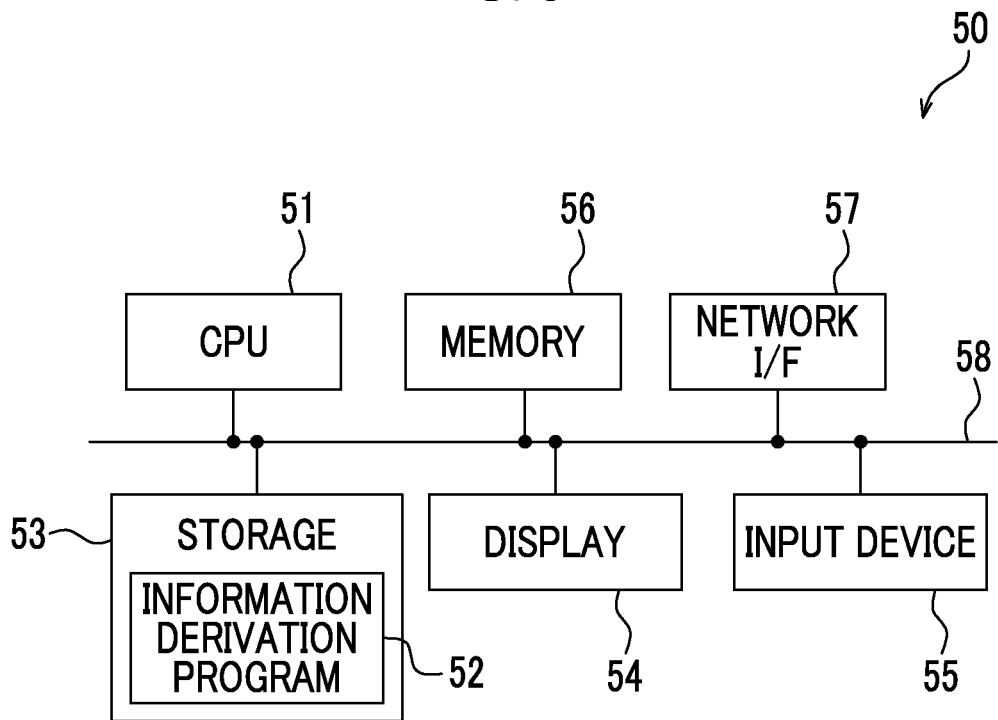
FIG. 6 is a diagram showing a schematic configuration of an information derivation device according to the first embodiment.

FIG. 6 is a schematic block diagram showing a configuration of the information derivation device according to the first embodiment. As shown in FIG. 6, the information derivation device 50 according to the first embodiment is a computer, such as a workstation, a server computer, and a personal computer, and includes a CPU 51, a non-volatile storage 53, and a memory 56 as a transitory storage region. In addition, the information derivation device 50 includes a display 54, such as a liquid crystal display, an input device 55 including a pointing device, such as a keyboard and a mouse, and a network I/F 57 connected to a network (not shown). The CPU 51, the storage 53, the display 54, the input device 55, the memory 56, and the network I/F 57 are connected to a bus 58.

Similar to the storage 13, the storage 53 is realized by the HDD, the SSD, the flash memory, and the like. An information derivation program 52 is stored in the storage 53 as the storage medium. The CPU 51 reads out the information derivation program 52 from the storage 53, expands the read out information derivation program 52 in the memory 56, and executes the expanded information derivation program 52.

Figure 7:
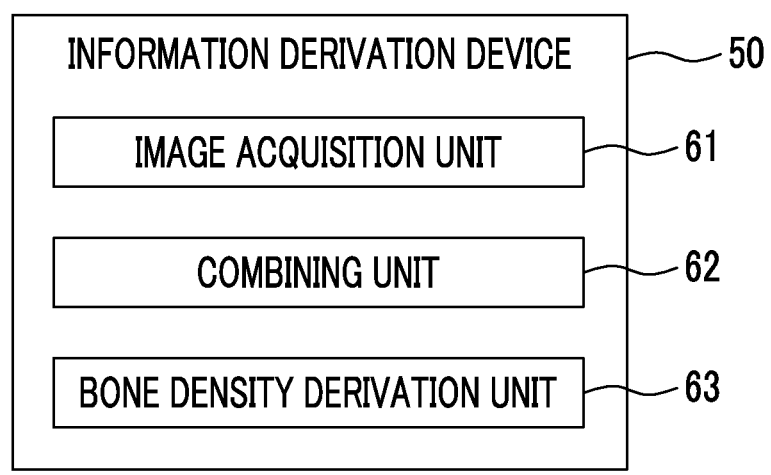
FIG. 7 is a diagram showing a functional configuration of the information derivation device according to the first embodiment.

Then, a functional configuration of the information derivation device according to the first embodiment will be described. FIG. 7 is a diagram showing the functional configuration of the information derivation device according to the first embodiment. As shown in FIG. 7, the information derivation device 50 according to the first embodiment comprises an image acquisition unit 61, a combining unit 62, and an emphasis image derivation unit 63. Further, the CPU 51 executes the information derivation program 52, so that the CPU 51 functions as the image acquisition unit 61, the combining unit 62, and the emphasis image derivation unit 63.

The image acquisition unit 61 acquires, from the image storage system 9, the CT image V0 for deriving the learning data 41. The image acquisition unit 61 may acquire the CT image V0 by causing the CT device 7 to image the subject H, in the same manner as the image acquisition unit 21 of the estimation device 10.

Figure 8:
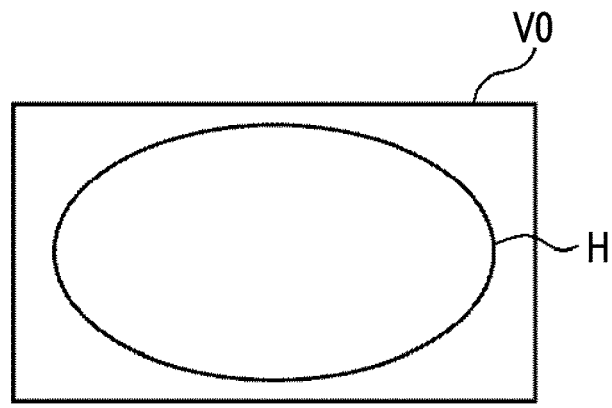
FIG. 8 is a diagram for describing derivation of a composite two-dimensional image.
Figure 8:
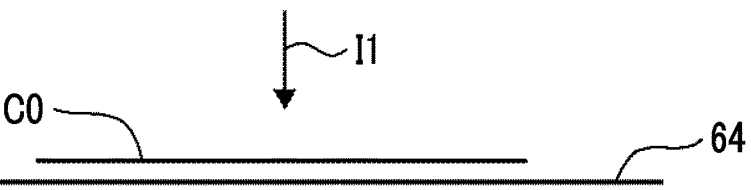

The combining unit 62 derives the composite two-dimensional image C0 representing the subject H by combining the CT image V0. FIG. 8 is a diagram for describing derivation of the composite two-dimensional image C0. Note that in FIG. 8, the three-dimensional CT image V0 is shown in two dimensions for the sake of description. As shown in FIG. 8, the subject H is included in a three-dimensional space represented by the CT image V0. The subject H includes a plurality of compositions of the bone part, the fat, the muscle, and the internal organs.

Here, the CT value V0(x,y,z) in each pixel of the CT image V0 can be represented by Expression (1) by using an attenuation coefficient pi of the composition in the pixel and an attenuation coefficient μw of water. (x,y,z) are coordinates representing pixel positions of the CT image V0. Note that, in the following description, the attenuation coefficient means the linear attenuation coefficient unless otherwise specified. The attenuation coefficient represents a degree (ratio) of the radiation attenuation due to absorption or scattering. The attenuation coefficient differs depending on a specific composition (density or the like) and the thickness (mass) of the structure through which radiation is transmitted.

$$V0(x,y,z)=(\mu i-\mu w)/\mu w \times 1000 \quad (1)$$

The attenuation coefficient μw of the water is known. Therefore, by solving Expression (1) for μi, the attenuation coefficient μi of each composition can be calculated as shown in Expression (2).

$$\mu i = V0(x,y,z) \times \mu w/1000 + \mu w \quad (2)$$

As shown in FIG. 8, the combining unit 62 virtually irradiates the subject H with the radiation having an irradiation dose I0, and derives the composite two-dimensional image C0 obtained by virtually detecting the radiation transmitted through the subject H by the radiation detector (not shown) installed on a virtual plane 64. Note that the irradiation dose I0 of the virtual radiation and the radiation energy are set depending on predetermined imaging conditions. In this case, a reaching dose I1(x,y) for each pixel of the composite two-dimensional image C0 is transmitted through one or more compositions in the subject H. Therefore, the reaching dose I1(x,y) can be derived by Expression (3) by using the attenuation coefficient μi of one or more compositions through which the radiation of the irradiation dose I0 is transmitted. Note that the reaching dose I1(x,y) is the pixel value of each pixel of the composite two-dimensional image C0.

$$I1(x,y)=I0 \times \exp(-\int \mu i \cdot dt) \quad (3)$$

Figure 9:
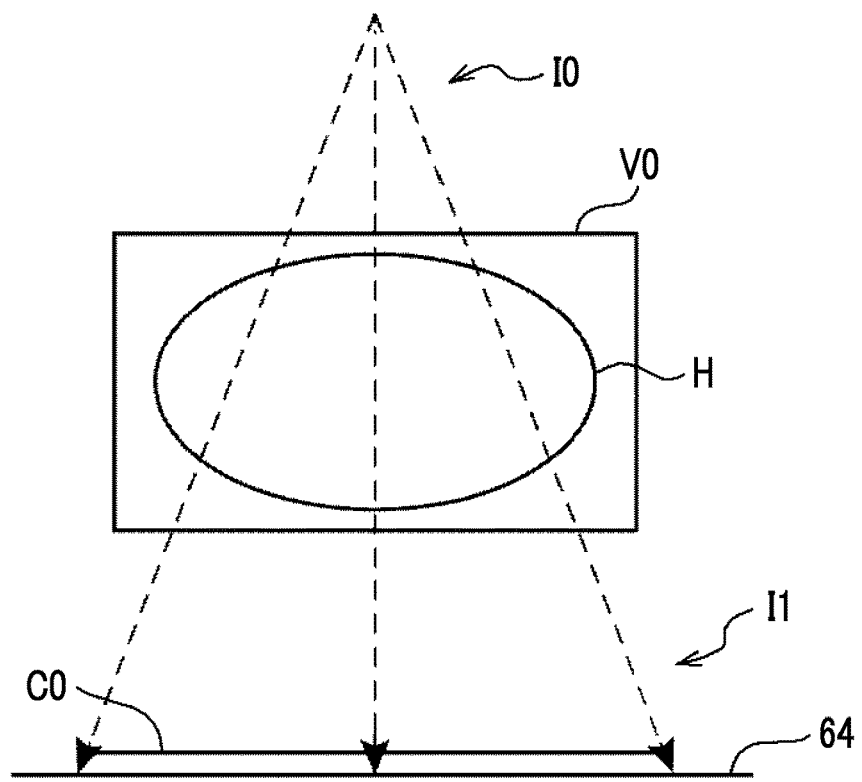
FIG. 9 is a diagram for describing the derivation of the composite two-dimensional image.

Note that in a case in which it is assumed that the radiation source to be irradiated is a plane light source, as the attenuation coefficient μi used in Expression (3), a value derived by Expression (2) from the CT value of the pixels arranged in the vertical direction shown in FIG. 8 need only be used. In addition, in a case in which it is assumed that the plane light source of the light source to be emitted is a point light source, as shown in FIG. 9, based on the geometric positional relationship between the point light source and each position on the virtual plane 64, the pixel on the path of the radiation reaching each pixel need only be specified and the attenuation coefficient derived from the CT value of the specified pixel by Expression (2) need only be used.

Figure 10:
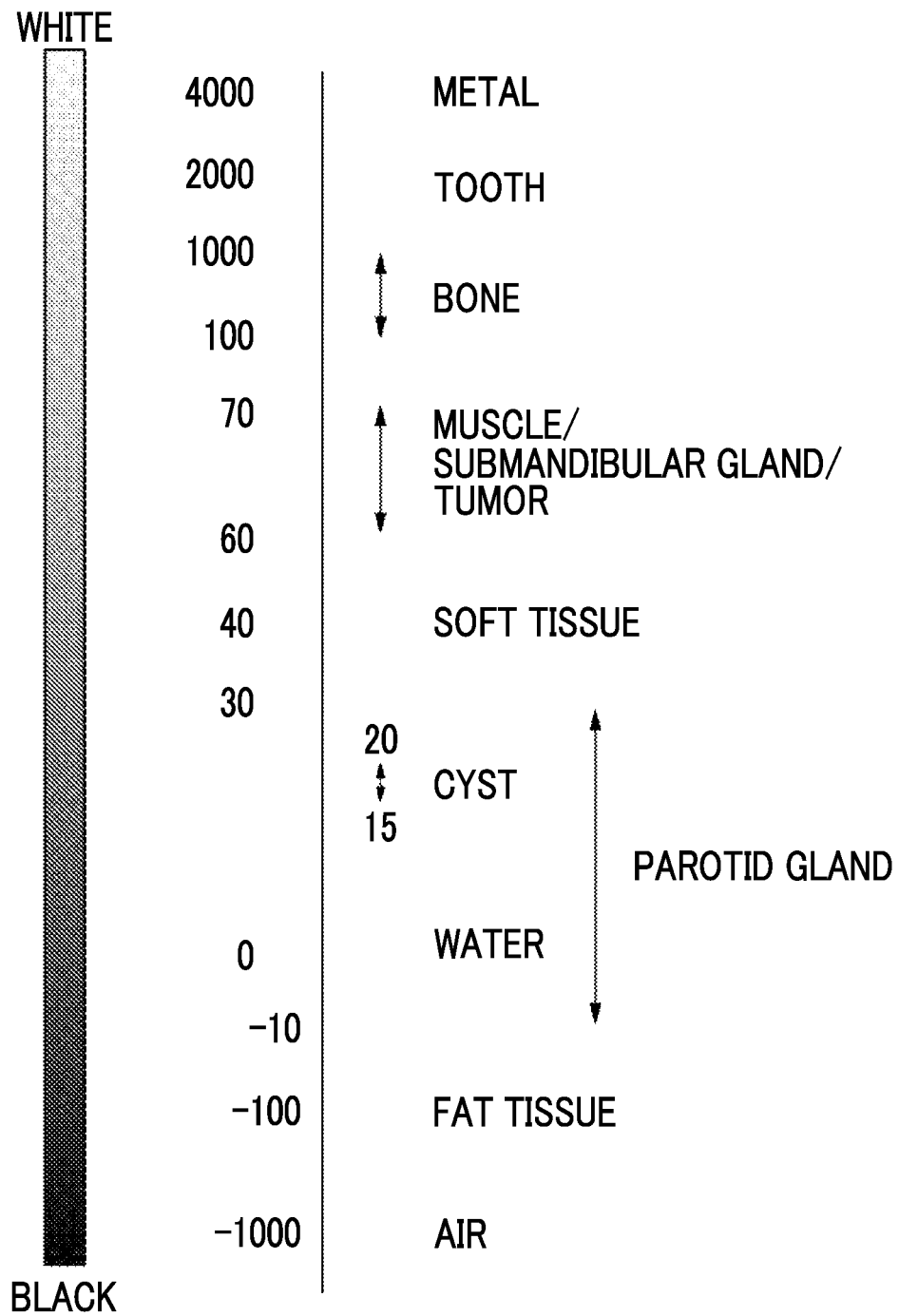
FIG. 10 is a diagram for describing a CT value.

The emphasis image derivation unit 63 derives the bone part image Gb in which the bone part of the subject is emphasized and the soft part image Gs in which the soft part is emphasized, by using the CT image V0. Here, description for the CT value will be made. FIG. 10 is a diagram for describing the CT value. The CT value is a numerical value of the X-ray absorbance in the human body. Specifically, as shown in FIG. 10, the CT value is determined depending on the composition constituting the human body, such as 0 for the water and −1000 (unit: HU) for the air.

The emphasis image derivation unit 63 first specifies the bone region in the CT image V0 based on the CT value of the CT image V0. Specifically, the region consisting of the pixels having the CT value of 100 to 1000 is specified as the bone region by the threshold value processing. Note that the bone region may be specified by using the learned neural network learned to detect the bone region from the CT image V0 instead of the threshold value processing. In addition, the bone region may be specified by displaying the CT image V0 on the display 54 and receiving designation of the bone region by a manual operation in the displayed CT image V0.

Figure 11:
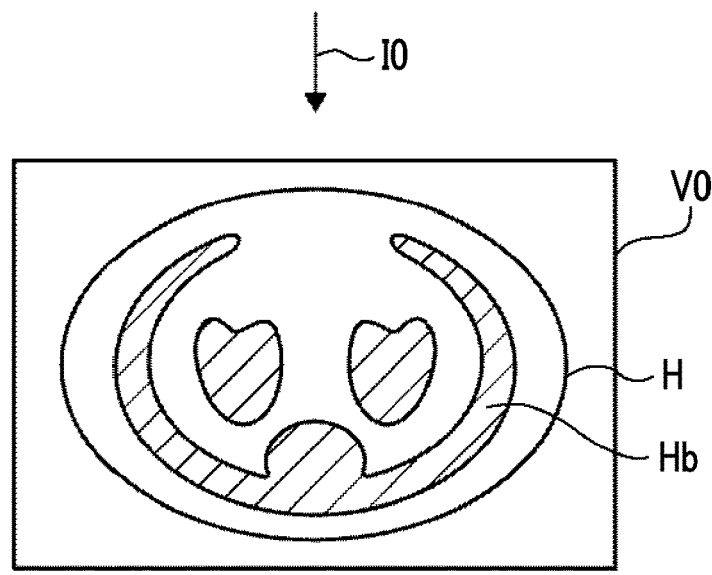
FIG. 11 is a diagram for describing derivation of a bone part image.
Figure 11:
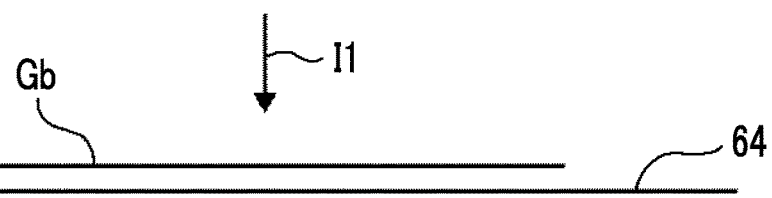
Figure 12:
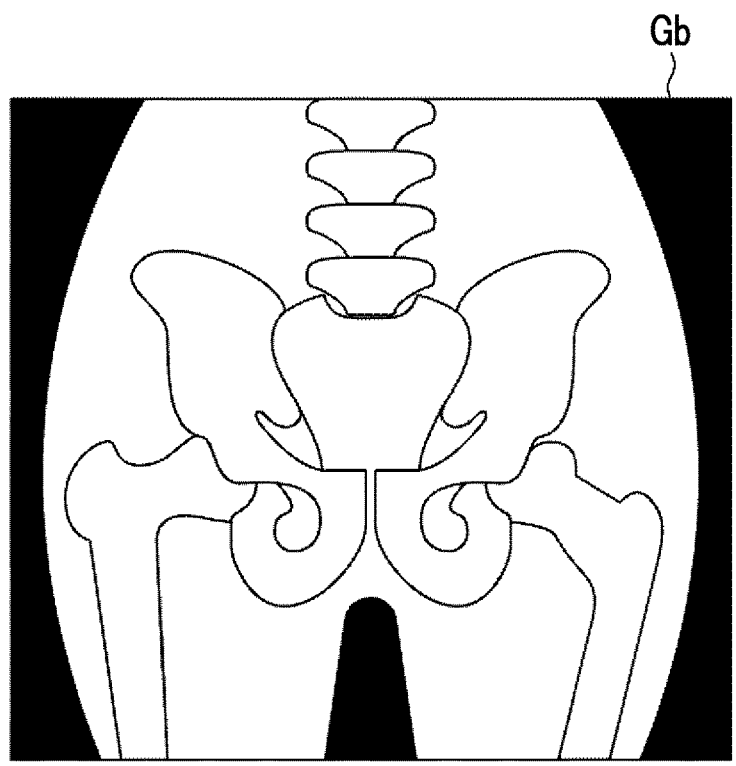
FIG. 12 is a diagram showing the bone part image.

Further, as shown in FIG. 11, the emphasis image derivation unit 63 projects the CT value of a bone region Hb in the subject H included in the CT image V0 onto the virtual plane 64 as in a case of deriving the composite two-dimensional image C0 to derive the bone part image Gb. The bone part image Gb is shown in FIG. 12.

In addition, the emphasis image derivation unit 63 specifies the soft region in the CT image V0 based on the CT value of the CT image V0. Specifically, the region consisting of the pixels having the CT value of −100 to 70 is specified as the soft region by the threshold value processing. Note that the soft region may be specified by using the learned neural network learned to detect the soft region from the CT image V0 instead of the threshold value processing. In addition, the soft region may be specified by displaying the CT image V0 on the display 54 and receiving designation of the soft region by an manual operation in the displayed CT image V0.

Figure 13:
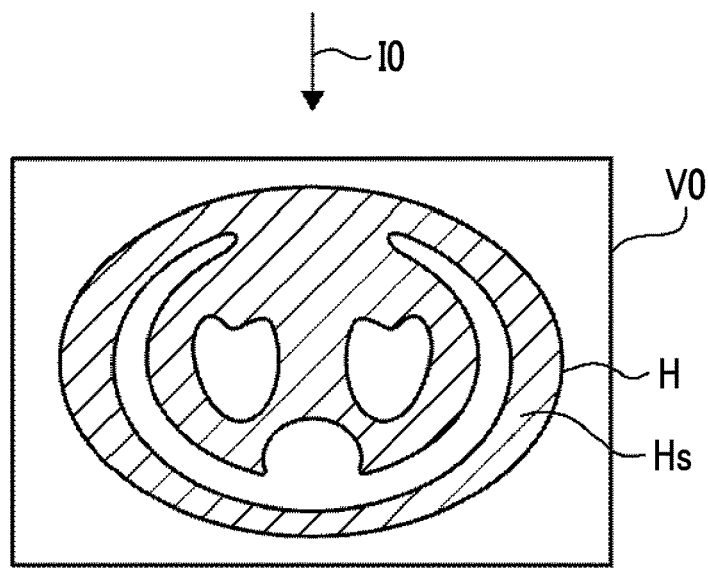
FIG. 13 is a diagram for describing derivation of a soft part image.
Figure 13:
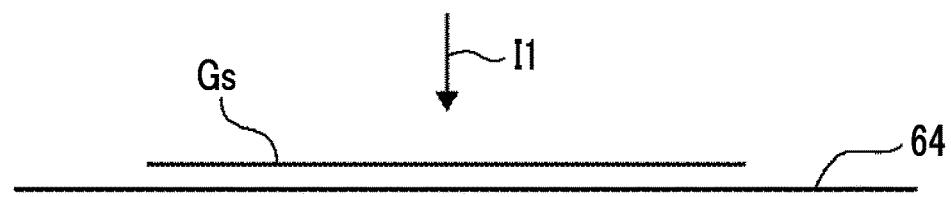
Figure 14:
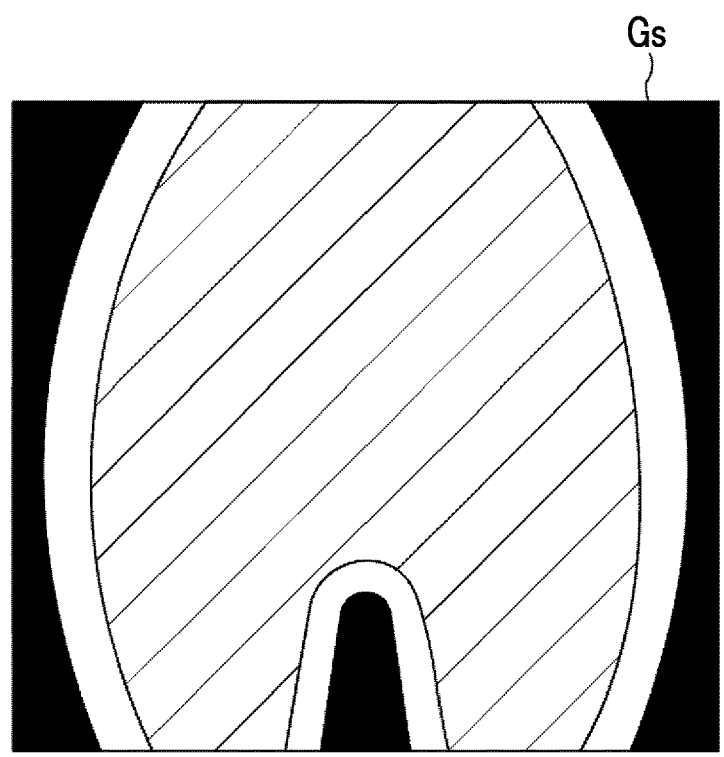
FIG. 14 is a diagram showing the soft part image.

Further, as shown in FIG. 13, the emphasis image derivation unit 63 projects the CT value of a soft region Hs in the subject H included in the CT image V0 onto the virtual plane 64 as in a case of deriving the composite two-dimensional image C0 to derive the soft part image Gs. The soft part image Gs is shown in FIG. 14.

The bone part image Gb and the soft part image Gs, which are used as the correct answer data 42, are derived at the same time as the time when the learning data 41 is acquired, and are transmitted to the image storage system 9. In the image storage system 9, the learning data 41 and the correct answer data 42 are stored in association with each other as the teacher data 40. Note that in order to improve the robustness of the learning, the teacher data 40 including, as learning data 41, an image obtained by performing at least one of enlargement/reduction, contrast change, movement, in-plane rotation, inversion, or noise addition on the same image may be additionally created and stored.

Figure 15:
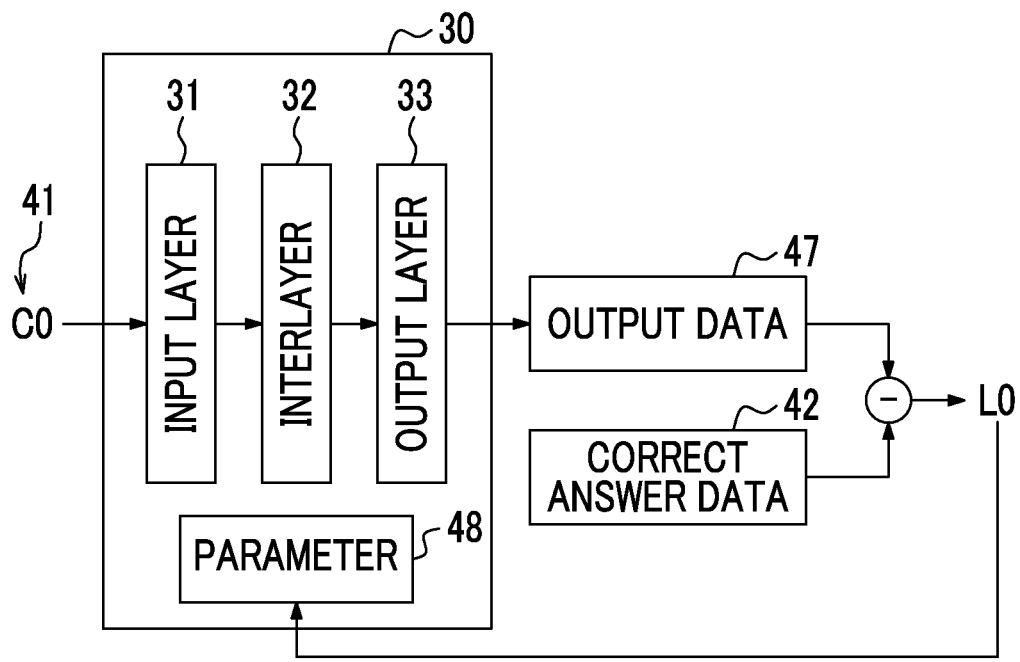
FIG. 15 is a diagram for describing learning of the neural network.

The description will be returned to the estimation device 10. The learning unit 24 learns the neural network by using a large amount of the teacher data 40. FIG. 15 is a diagram for describing learning of the neural network 30. In a case in which the neural network 30 is learned, the learning unit 24 inputs the learning data 41, that is, the composite two-dimensional image C0 to the input layer 31 of the neural network 30. Further, the learning unit 24 outputs the bone part image and the soft part image as output data 47 from the output layer 33 of the neural network 30. Further, the learning unit 24 derives a difference between the output data 47 and the correct answer data 42 as a loss L0. Note that the loss is derived between the bone part image of the output data 47 and the bone part image of the correct answer data 42, and between the soft part image of the output data and the soft part image of the correct answer data 42, respectively, and L0 is used as the reference numeral thereof.

The learning unit 24 learns the neural network 30 based on the loss L0. Specifically, the learning unit 24 adjusts a kernel coefficient in the convolutional layer 35, a weight of the bond between the layers, a weight of the bond in the fully bonded layer 37, and the like (hereinafter referred to as a parameter 48) such that the loss L0 is reduced. For example, an error backpropagation method can be used as a method for adjusting the parameter 48. The learning unit 24 repeats the adjustment of the parameter 48 until the loss L0 is equal to or smaller than a predetermined threshold value. As a result, in a case in which the simple radiation image G0 is input, the parameter 48 is adjusted so as to output the bone part image Gb and the soft part image Gs of the input simple radiation image G0, and the learned neural network 23A is constructed. The constructed learned neural network 23A is stored in the storage 13.

Figure 16:
FIG. 16 is a conceptual diagram of processing performed by a learned neural network.

FIG. 16 is a conceptual diagram of processing performed by the learned neural network 23A. As shown in FIG. 16, in a case in which the simple radiation image G0 of a patient is input to the learned neural network 23A constructed as described above, the learned neural network 23A outputs the bone part image Gb and the soft part image Gs for the input simple radiation image G0.

Figure 17:
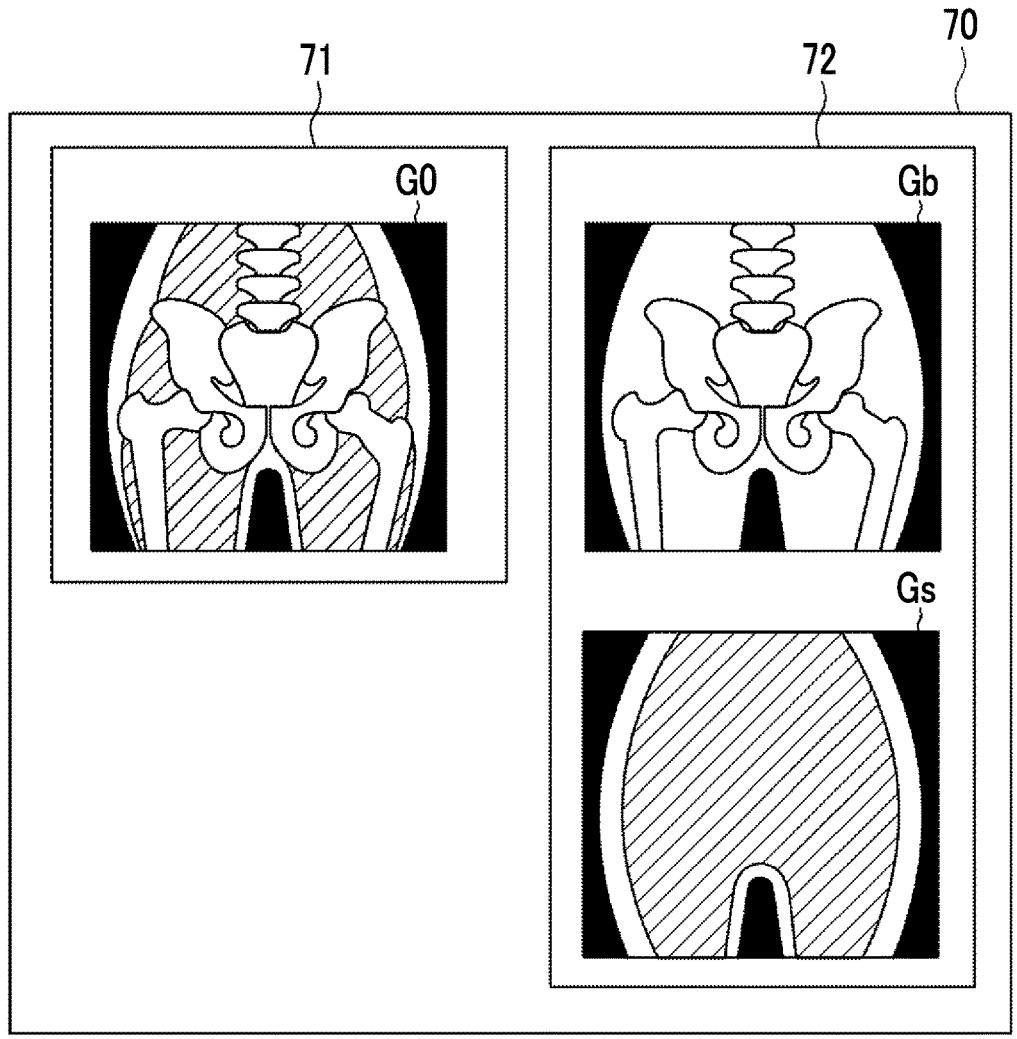
FIG. 17 is a diagram showing a display screen of a result of estimation.

The display controller 25 displays the results of estimation of the bone part image Gb and the soft part image Gs estimated by the estimation unit 23 on the display 14. FIG. 17 is a diagram showing a display screen of the result of estimation. As shown in FIG. 17, the display screen 70 has a first image display region 71 and a second image display region 72. The simple radiation image G0 of the subject H is displayed in the first image display region 71. In addition, in the second image display region 72, the bone part image Gb and the soft part image Gs estimated by the estimation unit 23 are displayed.

Figure 18:
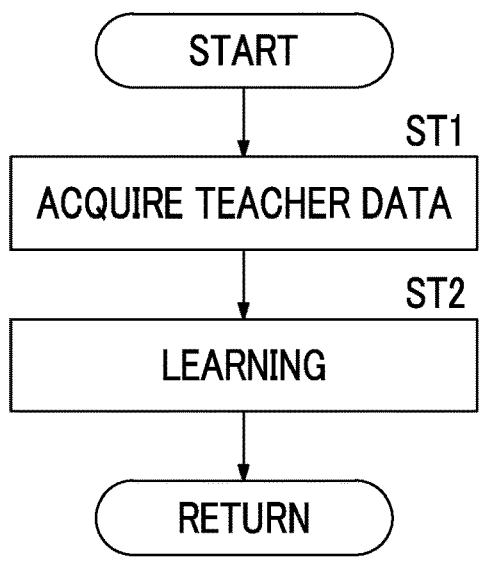
FIG. 18 is a flowchart of learning processing performed in the first embodiment.

Then, the processing performed in the first embodiment will be described. FIG. 18 is a flowchart showing learning processing performed in the first embodiment. First, the information acquisition unit 22 acquires the teacher data 40 from the image storage system 9 (step ST1), and the learning unit 24 inputs the learning data 41 included in the teacher data 40 to the neural network 30 to output the bone part image Gb and the soft part image Gs and learns the neural network 30 by using the loss L0 based on the difference from the correct answer data 42 (step ST2), and the processing returns to step ST1. Further, the learning unit 24 repeats the processing of steps ST1 and ST2 until the loss L0 reaches the predetermined threshold value, and terminates the learning processing. Note that the learning unit 24 may terminate the learning processing by repeating the learning a predetermined number of times. As a result, the learning unit 24 constructs the learned neural network 23A.

Figure 19:
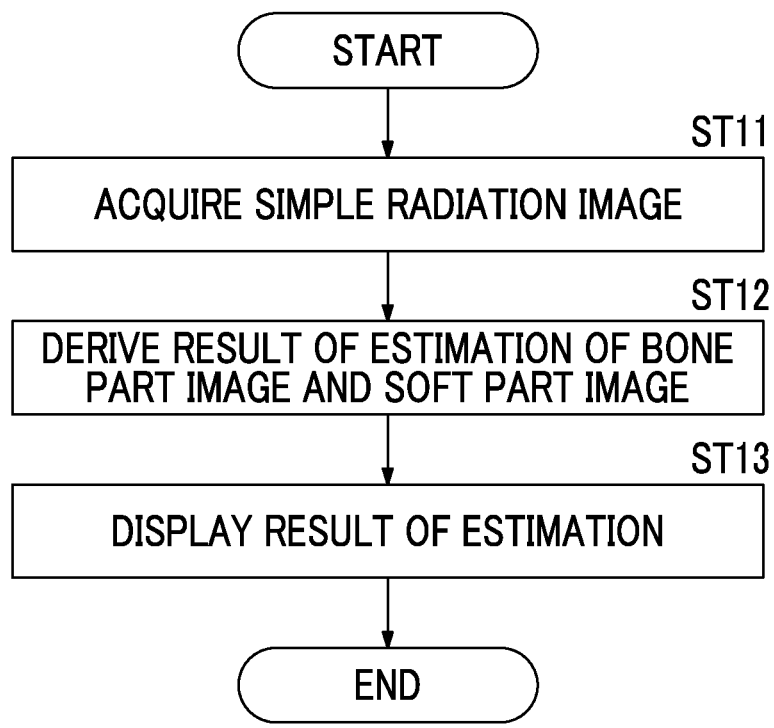
FIG. 19 is a flowchart showing estimation processing performed in the first embodiment.

Then, estimation processing in the first embodiment will be described. FIG. 19 is a flowchart showing the estimation processing in the first embodiment. Note that the simple radiation image G0 is acquired by the imaging and stored in the storage 13. In a case in which an instruction for starting the processing is input from the input device 15, the image acquisition unit 21 acquires the simple radiation image G0 from the storage 13 (step ST11). Then, the estimation unit 23 derives the results of estimation of the bone part image Gb and the soft part image Gs from the simple radiation image G0 (step ST12). Further, the display controller 25 displays the results of estimation of the bone part image Gb and the soft part image Gs derived by the estimation unit 23 on the display 14 together with the simple radiation image G0 (step ST13), and terminates the processing.

As described above, in the present embodiment, by using the learned neural network 23A constructed by performing learning with the composite two-dimensional image C0 derived from the CT image V0 and the bone part image Gb and the soft part image Gs derived from the CT image V0 as the teacher data, the results of estimation of the bone part image Gb and the soft part image Gs for the simple radiation image G0 are derived. Here, in the present embodiment, the composite two-dimensional image C0 derived from the CT image V0 and the bone part image Gb and the soft part image Gs derived from the CT image V0 are used for learning the neural network. Therefore, the learned neural network 23A can derive the results of estimation of the bone part image Gb and the soft part image Gs from the simple radiation image G0 with higher accuracy as compared with a case in which one radiation image and the information relating to the bone part image Gb and the soft part image Gs, which are derived from the radiation image, are used as the teacher data. Therefore, according to the present embodiment, the results of estimation of the bone part image Gb and the soft part image Gs can be derived with higher accuracy.

Note that in the first embodiment, the results of estimation of the bone part image Gb and the soft part image Gs are derived, but the present disclosure is not limited to this. The result of estimation of any one of the bone part image Gb or the soft part image Gs may be derived. In this case, the learned neural network 23A need only be constructed by learning with the teacher data in which the correct answer data is any one of the bone part image Gb or the soft part image Gs.

In addition, in the first embodiment described above, the results of estimation of the bone part image Gb and the soft part image are derived from the simple radiation image G0, but the present disclosure is not limited to this. For example, the results of estimation of the muscle image and the fat image may be derived. Hereinafter, this case will be described as a second embodiment.

The configuration of an estimation device and an information derivation device according to the second embodiment is the same as the configuration of the estimation device 10 and the information derivation device 50 according to the first embodiment, only the processing to be performed is different, and thus the detailed description thereof is omitted. In the second embodiment, the emphasis image derivation unit 63 of the information derivation device 50 derives the muscle image Gm and the fat image Gf instead of deriving the bone part image Gb and the soft part image Gs as the correct answer data 42.

In the second embodiment, the emphasis image derivation unit 63 first specifies the muscle region in the CT image V0 based on the CT value of the CT image V0. Specifically, a region consisting of the pixels having the CT value of 60 to 70 is specified as the muscle region by the threshold value processing. Note that the muscle region may be specified by using the learned neural network learned to detect the muscle region from the CT image V0 instead of the threshold value processing. In addition, the muscle region may be specified by displaying the CT image V0 on the display 54 and receiving designation of the muscle region by the manual operation in the displayed CT image V0.

Figure 20:
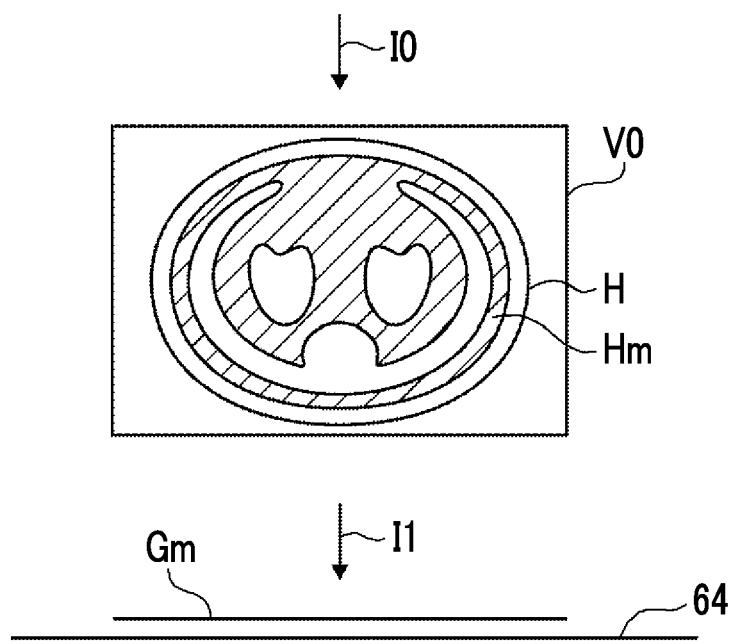
FIG. 20 is a diagram for describing derivation of a muscle image.
Figure 21:
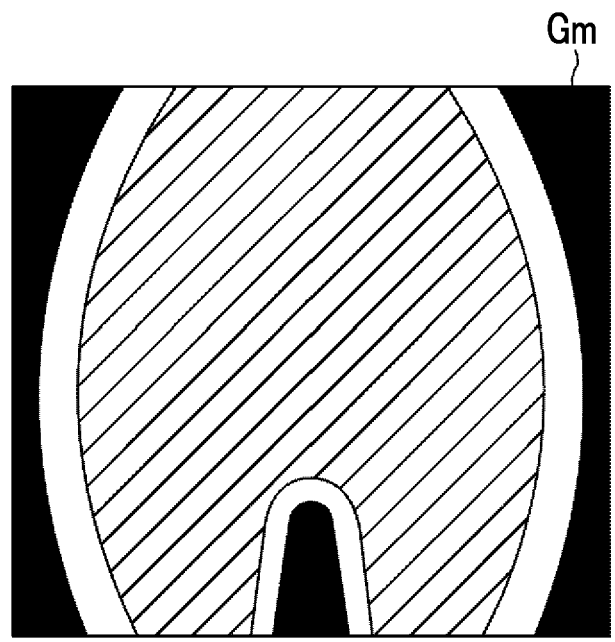
FIG. 21 is a diagram showing the muscle image.

Further, as shown in FIG. 20, the emphasis image derivation unit 63 projects the CT value of a muscle region Hm in the subject H included in the CT image V0 onto the virtual plane 64 as in a case of deriving the composite two-dimensional image C0 to derive the muscle image Gm. The muscle image Gm is shown in FIG. 21.

In addition, the emphasis image derivation unit 63 specifies the fat region in the CT image V0 based on the CT value of the CT image V0. Specifically, the region consisting of the pixels having the CT value of −100 to −10 is specified as the fat region by the threshold value processing. Note that the fat region may be specified by using the learned neural network learned to detect the fat region from the CT image V0 instead of the threshold value processing. In addition, the fat region may be specified by displaying the CT image V0 on the display 54 and receiving designation of the fat region by the manual operation in the displayed CT image V0.

Figure 22:
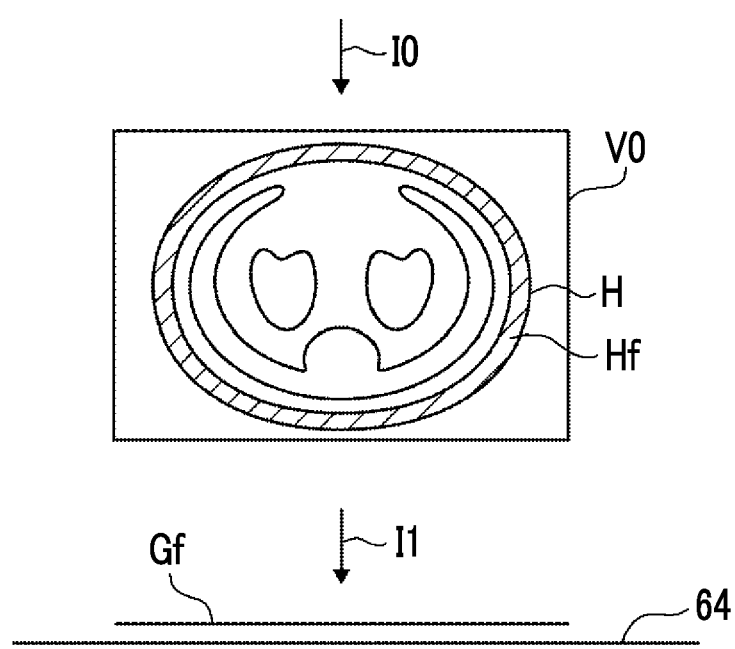
FIG. 22 is a diagram for describing derivation of a fat image.
Figure 23:
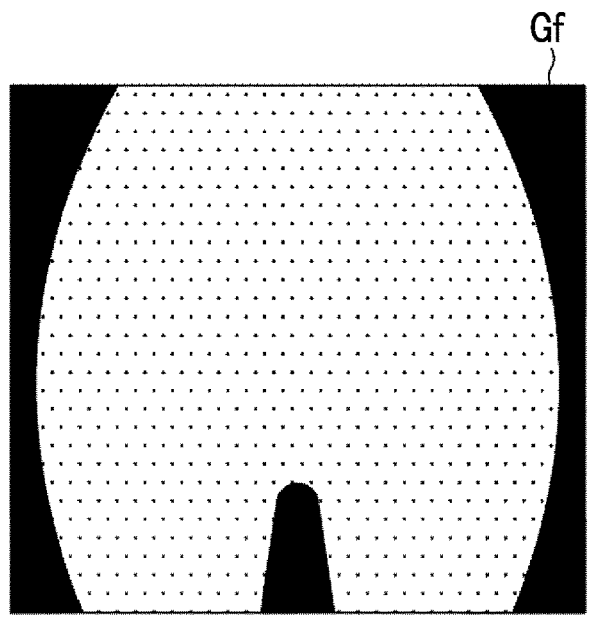
FIG. 23 is a diagram showing the fat image.

Further, as shown in FIG. 22, the emphasis image derivation unit 63 projects the CT value of a fat region Hf in the subject H included in the CT image V0 onto the virtual plane 64 as in a case of deriving the composite two-dimensional image C0 to derive the fat image Gf. The fat image Gf is shown in FIG. 23.

Figure 24:
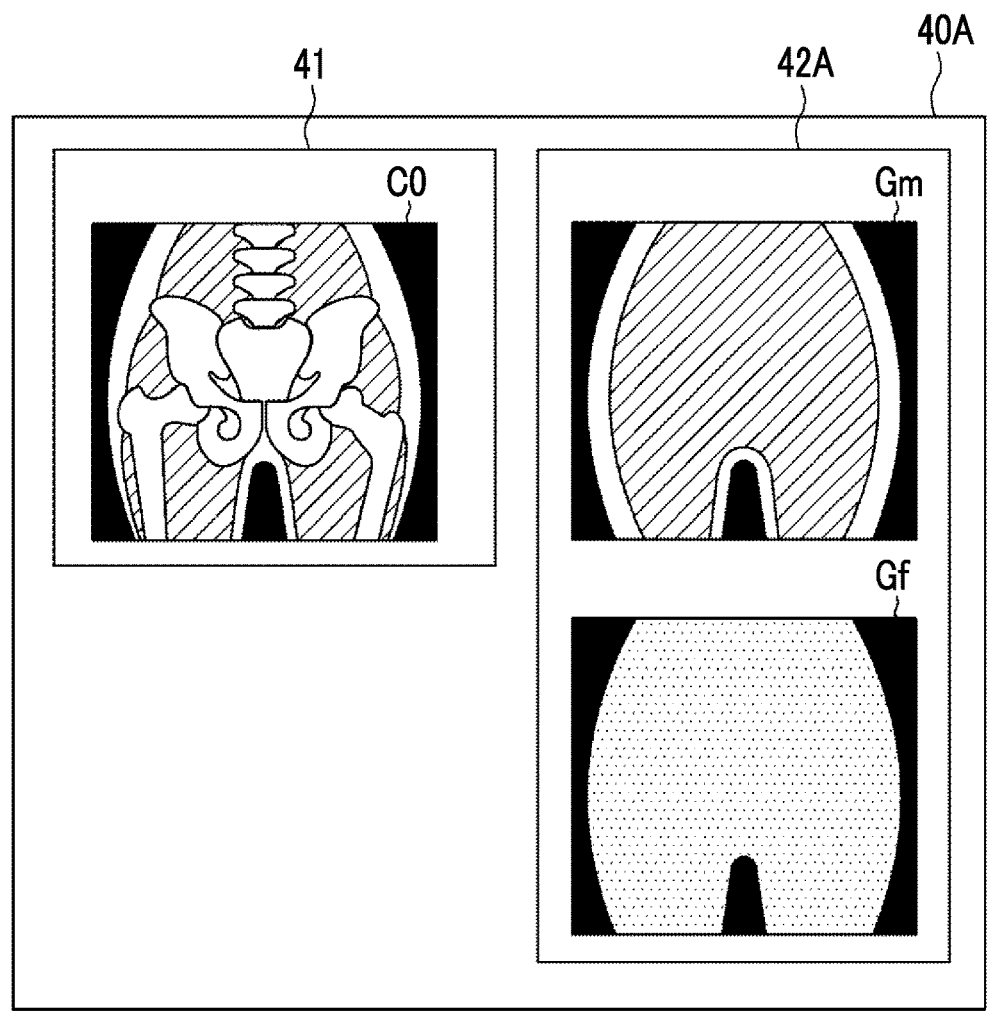
FIG. 24 is a diagram showing another example of the teacher data.

In the second embodiment, the muscle image Gm and the fat image Gf, which are derived by the information derivation device 50, are used as the correct answer data of the teacher data. FIG. 24 is a diagram showing the teacher data derived in the second embodiment. As shown in FIG. 24, the teacher data 40A consists of the learning data 41 including the composite two-dimensional image C0, and correct answer data 42A including the muscle image Gm and the fat image Gf.

By learning the neural network by using the teacher data 40A shown in FIG. 24, it is possible to construct the learned neural network 23A that outputs the muscle image Gm and the fat image Gf as the results of estimation in a case in which the simple radiation image G0 is input.

Note that in the second embodiment, the results of estimation of the muscle image Gm and the fat image Gf are derived, but the present disclosure is not limited to this. The result of estimation of any one of the muscle image Gm or the fat image Gf may be derived. In this case, the learned neural network 23A need only be constructed by performing learning with the teacher data in which the correct answer data is any one of the muscle image Gm or the fat image Gf.

Figure 25:
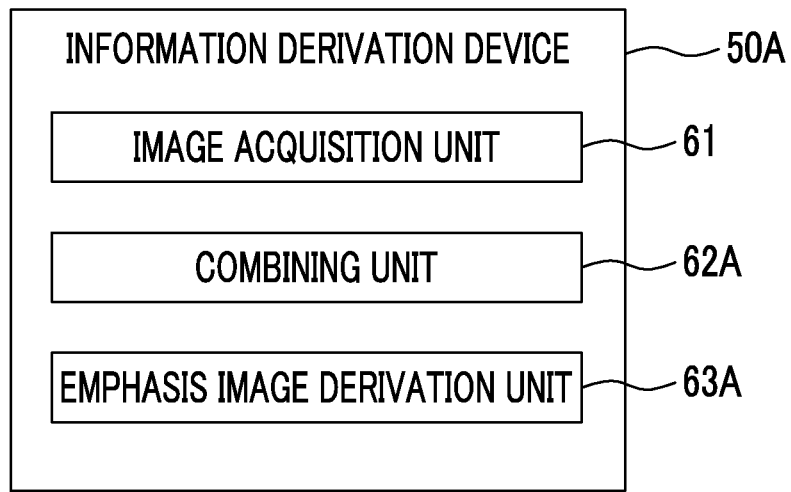
FIG. 25 is a diagram showing a functional configuration of an information derivation device according to a third embodiment.

Then, a third embodiment of the present disclosure will be described. FIG. 25 is a diagram showing a functional configuration of an information derivation device according to the third embodiment. Note that in FIG. 25, the same reference numerals are assigned to the same configurations as those in FIG. 7, and the detailed description thereof will be omitted. In the first and second embodiments, the emphasis image for learning (that is, the bone part image Gb, the soft part image Gs, the muscle image Gm, and the fat image Gf), which is the correct answer data 42, is derived by projecting the specific composition in the subject H in the CT image V0. In the third embodiment, the emphasis image for learning is derived by deriving two composite two-dimensional images simulating the low-energy radiation image and the high-energy radiation image from the CT image V0 and performing the weighting subtraction on the two derived composite two-dimensional images.

Therefore, as shown in FIG. 25, an information derivation device 50A according to the third embodiment further comprises a combining unit 62A and an emphasis image derivation unit 63A with respect to the information derivation device 50 according to the first embodiment. Note that in the following description, the bone part image Gb and the soft part image Gs will be derived as the emphasis image for learning.

Figure 26:
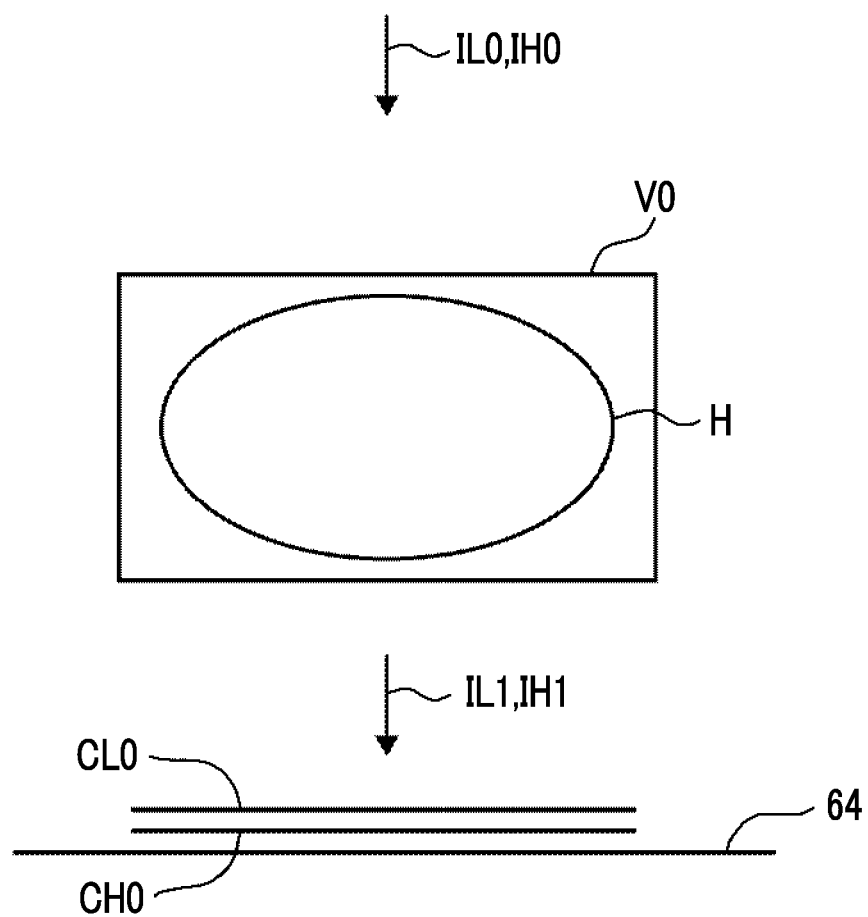
FIG. 26 is a diagram for describing the derivation of the composite two-dimensional image in the third embodiment.

In the third embodiment, as shown in FIG. 26, the combining unit 62A virtually irradiates the subject H with the radiation having two types of doses IL0 and IH0 having different energy distributions, and derives two composite two-dimensional images CL0 and CH0 obtained by virtually detecting the radiation having the transmitted doses IL1 and IH1 transmitted through the subject H by the radiation detector installed in the virtual plane 64. The composite two-dimensional image CL0 corresponds to the radiation image of the subject H due to the low-energy radiation including so-called soft rays. The composite two-dimensional image CH0 corresponds to the radiation image of the subject H due to the high-energy radiation from which soft rays are removed.

The emphasis image derivation unit 63A specifies the bone region and the soft region in the composite two-dimensional images CL0 and CH0. The pixel values of the bone region and the soft region are clearly different from each other in the composite two-dimensional images CL0 and CH0. Therefore, the emphasis image derivation unit 63A specifies the bone region and the soft region in the composite two-dimensional images CL0 and CH0 by the threshold value processing. Instead of the threshold value processing, the bone region and the soft region may be specified by using the learned neural network, which is learned to detect the bone region and the soft region in the composite two-dimensional images CL0 and CH0. In addition, the bone region and the soft region may be specified by displaying the composite two-dimensional images CL0 and CH0 on the display 54, and receiving designation of the bone region and the soft region by the manual operation in the displayed composite two-dimensional images CL0 and CH0.

In the third embodiment, the emphasis image derivation unit 63A derives the bone part image Gb and the soft part image Gs by performing the weighting subtraction on the two composite two-dimensional images. Therefore, for the soft regions in the two composite two-dimensional images CL0 and CH0, the emphasis image derivation unit 63A derives a ratio CLs(x,y)/CHs(x,y) between the pixel value CLs(x,y) of the composite two-dimensional image CL0 corresponding to the low-energy image and the pixel value CHs(x,y) of the composite two-dimensional image CH0 which is the high-energy image, as the weighting coefficient α in a case of performing the weighting subtraction for deriving the bone part image Gb. Note that the ratio CLs1(x,y)/CHs2(x,y) represents a ratio $\mu ls/\mu hs$ of an attenuation coefficient $\mu ls$ for the low-energy radiation to an attenuation coefficient $\mu hs$ for the high-energy radiation in the soft part.

In addition, for the bone regions in the two composite two-dimensional images CL0 and CH0, the emphasis image derivation unit 63A derives a ratio CLb(x,y)/CHb(x,y) between the pixel value CLb(x,y) of the composite two-dimensional image CL0 corresponding to the low-energy image and the pixel value CHb(x,y) of the composite two-dimensional image CH0 corresponding to the high-energy image, as the weighting coefficient β in a case of performing the weighting subtraction for deriving the soft part image Gs. Note that the ratio CLb1(x,y)/CHb2(x,y) represents a ratio $\mu lb/\mu hb$ of an attenuation coefficient $\mu lb$ for the low-energy radiation to an attenuation coefficient $\mu hb$ for the high-energy radiation in the bone part.

In the third embodiment, the emphasis image derivation unit 63A derives the bone part image Gb and the soft part image Gs by using the derived weighting coefficients α and β to perform the weighting subtraction on the composite two-dimensional images CL0 and CH0 by Expression (4) and Expression (5).

$$Gb(x,y) = \alpha \cdot CH0(x,y) - CL0(x,y) \quad (4)$$

$$Gs(x,y) = CH0(x,y) - \beta \times CH0(x,y) \quad (5)$$

Note that in each of the embodiments described above, the estimation device 10 learns the neural network to construct the learned neural network 23A, but the present disclosure is not limited to this. The learned neural network 23A constructed in a device other than the estimation device 10 may be used for the estimation unit 23 of the estimation device 10 in the present embodiment.

In addition, in each of the embodiments described above, the processing for estimating the emphasis image is performed by using the radiation image acquired by the system that images the subject H by using the radiation detector 5, it is needless to say that the technology of the present disclosure can be applied to even in a case in which the radiation image are acquired by using an accumulative phosphor sheet instead of the radiation detector.

In addition, the radiation in the embodiments described above is not particularly limited, and α-rays or γ-rays can be used in addition to X-rays.

In addition, in the embodiments described above, various processors shown below can be used as the hardware structures of processing units that execute various pieces of processing, such as the image acquisition unit 21, the information acquisition unit 22, the estimation unit 23, the learning unit 24, and the display controller 25 of the estimation device 10, and the image acquisition unit 61, the combining unit 62, and the emphasis image derivation unit 63 of the information derivation device 50. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

What is claimed is:

1. An estimation device comprising:
at least one processor,
wherein the processor functions as a learned neural network that derives a result of estimation of at least one emphasis image in which a specific composition of a subject including a plurality of compositions is emphasized from a simple two-dimensional image acquired by simply imaging the subject, and
the learned neural network is learned by using, as teacher data, a composite two-dimensional image representing the subject, which is derived by combining a three-dimensional CT image of the subject, and an emphasis image for learning in which the specific composition of the subject is emphasized, which is derived from the CT image.

2. The estimation device according to claim 1, wherein the composite two-dimensional image is derived by deriving an attenuation coefficient of radiation for a composition at each position on a three-dimensional space, and projecting the CT image in a predetermined direction based on the attenuation coefficient.

3. The estimation device according to claim 1, wherein the emphasis image for learning is derived by specifying a region of the specific composition in the CT image and projecting the CT image having the region of the specific composition in a predetermined direction.

4. The estimation device according to claim 1, wherein the emphasis image for learning is derived by performing weighting subtraction on two composite two-dimensional images simulating imaging of the subject with radiation having different energy distributions, which are derived by projecting the CT image in a predetermined direction.

5. The estimation device according to claim 1, wherein the specific composition is at least one of a soft part, a bone part, a muscle, or a fat of the subject.

6. An estimation method comprising:
using a learned neural network that derives a result of estimation of at least one emphasis image in which a specific composition of a subject including a plurality of compositions is emphasized from a simple radiation image acquired by simply imaging the subject to derive the at least one emphasis image in which the specific composition of the subject is emphasized from the simple radiation image,
wherein the learned neural network is learned by using, as teacher data, a composite two-dimensional image representing the subject, which is derived by combining a three-dimensional CT image of the subject, and an emphasis image for learning in which the specific composition of the subject is emphasized, which is derived from the CT image.

7. A non-transitory computer-readable storage medium that stores an estimation program causing a computer to execute a procedure comprising:
using a learned neural network that derives a result of estimation of at least one emphasis image in which a specific composition of a subject including a plurality of compositions is emphasized from a simple radiation image acquired by simply imaging the subject to derive the at least one emphasis image in which the specific composition of the subject is emphasized from the simple radiation image, wherein the learned neural network is learned by using, as teacher data, a composite two-dimensional image representing the subject, which is derived by combining a three-dimensional CT image of the subject, and an emphasis image for learning in which the specific composition of the subject is emphasized, which is derived from the CT image.

* * * * *